US00PP16724P2

(12) United States Plant Patent
Miyazaki et al.

(10) Patent No.: US PP16,724 P2
(45) Date of Patent: Jun. 27, 2006

(54) ***PHLOX* PLANT NAMED 'SUNPHLOHO'**

(50) Latin Name: *Phlox drummondii*
Varietal Denomination: Sunphloho

(75) Inventors: Kiyoshi Miyazaki, Shiga (JP); Tomoya Misato, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 61 days.

(21) Appl. No.: 11/091,831

(22) Filed: Mar. 28, 2005

(51) Int. Cl.
*A01H 5/00* (2006.01)

(52) U.S. Cl. ..... Plt./320

(58) Field of Classification Search ..... Plt./320
See application file for complete search history.

*Primary Examiner*—Anne Marie Grunberg
(74) *Attorney, Agent, or Firm*—C. A. Whealy

(57) ABSTRACT

A new and distinct cultivar of *Phlox* plant named 'Sunphloho', characterized by its upright, outwardly spreading and uniformly mounded plant habit; freely branching and vigorous growth habit; white-colored flowers; freely and continuous flowering habit; tolerance to high temperatures; and good garden performance.

1 Drawing Sheet

Botanical designation: *Phlox drummondii.*
Cultivar denomination: 'Sunphloho'.

BACKGROUND OF THE INVENTION

The present Invention relates to a new and distinct cultivar of *Phlox* plant, botanically known as *Phlox drummondii*, and hereinafter referred to by the cultivar name Sunphloho.

The new *Phlox* is a product of a planned breeding program conducted by the Inventors in Higashiomi, Shiga, Japan. The objective of the breeding program was to create new compact *Phlox* cultivars with attractive flower coloration.

The new *Phlox* originated from a cross-pollination made by the Inventors in June, 2000 in Higashiomi, Shiga, Japan of a proprietary selection of *Phlox drummondii* identified as code number 01Ph-13b, not patented, as the female, or seed, parent with a proprietary selection of *Phlox drummondii* identified as code number 01Ph-13a, not patented, as the male, or pollen, parent. The new *Phlox* was discovered and selected by the Inventors as a flowering plant within the progeny of the stated cross-pollination in a controlled environment in Higashiomi, Shiga, Japan.

Asexual reproduction of the new cultivar by terminal cuttings at Higashiomi, Shiga, Japan since October, 2003, has shown that the unique features of this new *Phlox* are stable and reproduced true to type in successive generations.

SUMMARY OF THE INVENTION

Plants of the cultivar Sunphloho have not been observed under all possible environmental conditions. The phenotype may vary somewhat with variations in environment such as temperature and light level without, however, any variance in genotype.

The following traits have been repeatedly observed and are determined to be the unique characteristics of 'Sunphloho'. These characteristics in combination distinguish 'Sunphloho' as a new and distinct cultivar of *Phlox:*

1. Upright, outwardly spreading and mounded plant habit.
2. Freely branching and vigorous growth habit.

3. White-colored flowers.
4. Freely and continuous flowering habit.
5. Tolerant to high temperatures.
6. Good garden performance.

Plants of the new *Phlox* can be compared to plants of the female parent selection. In side-by-side comparisons conducted in Higashiomi, Shiga, Japan, plants of the new *Phlox* differed from plants of the female parent selection in the following characteristics:

1. Plants of the new *Phlox* were more vigorous than plants of the female parent selection.
2. Plants of the new *Phlox* were larger and had longer internodes than plants of the female parent selection.

Plants of the new *Phlox* can be compared to plants of the male parent selection. In side-by-side comparisons conducted in Higashiomi, Shiga, Japan, plants of the new *Phlox* differed from plants of the male parent selection in the following characteristics:

1. Plants of the new *Phlox* were more compact than plants of the male parent selection.
2. Plants of the new *Phlox* did not produce seeds whereas plants of the male parent selection produced seeds.

Plants of the new *Phlox* can also be compared to plants of the *Phlox drummondii* cultivar Sunphlopin, disclosed in U.S. Plant patent application Ser. No. 11/041,621. In side-by-side comparisons conducted in Higashiomi, Shiga, Japan, plants of the new *Phlox* differed from plants of the cultivar Sunphlopin in the following characteristics:

1. Plants of the new *Phlox* were taller and broader than plants of the cultivar Sunphlopin.
2. Plants of the new *Phlox* had longer internodes than plants of the cultivar Sunphlopin.
3. Plants of the new *Phlox* had longer leaves than plants of the cultivar Sunphlopin.
4. Plants of the new *Phlox* and the cultivar Sunphlopin differed in petal coloration.
5. Plants of the new *Phlox* had shorter pedicels than plants of the cultivar Sunphlopin.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new *Phlox*.

The photograph at the top of the sheet is a side perspective view of a typical plant of 'Sunphloho'.

The photograph at the bottom of the sheet is a close-up view of typical flowers and leaves of 'Sunphloho'.

DETAILED BOTANICAL DESCRIPTION

The aforementioned photographs, following observations and measurements describe plants grown in Higashiomi, Shiga, Japan in an outdoor nursery and under commercial production practices during the summer. Plants were grown in 15-cm containers and were about four months old when the photographs and description were taken. During the production of the plants, day temperatures averaged 22° C. and night temperatures averaged 12° C. Plants were pinched one time in the spring. In the following description, color references are made to The Royal Horticultural Society Colour Chart, 2001 Edition, except where general terms of ordinary dictionary significance are used.

Botanical classification: *Phlox drummondii* cultivar Sunphloho.

Parentage:

*Female, or seed, parent.*—Proprietary selection of *Phlox drummondii* identified as code number '01Ph-13b', not patented.

*Male, or pollen, parent.*—Proprietary selection of *Phlox drummondii* identified as code number '01Ph-13a', not patented.

Propagation:

*Type.*—By terminal cuttings.

*Time to initiate roots.*—About two to three weeks at 20 to 25° C.

*Time to produce a rooted plant.*—About one to two months at 20 to 25° C.

*Root description.*—Fine, fibrous, fleshy; ivory to pale brown in color.

*Rooting habit.*—Freely branching.

Plant description:

*Plant form/habit.*—Upright, outwardly spreading and mounded plant habit; broadly inverted triangle; vigorous growth habit. Freely branching habit, dense and bushy growth habit.

*Plant height.*—About 20.2 cm.

*Plant width (spread).*—About 40.6 cm.

*Lateral branches.*—Length: About 18.6 cm. Diameter: About 1.8 mm. Internode length: About 2 cm. Strength: Strong. Texture: Pubescent. Color: 144A.

*Foliage description.*—Arrangement: Alternate, simple; sessile. Length: About 3.8 cm. Width: About 1.3 cm. Shape: Lanceolate. Apex: Acute. Base: Obtuse. Margin: Entire. Texture, upper and lower surfaces: Pubescent. Venation pattern: Pinnate; reticulate. Color: Developing and fully expanded leaves, upper surface: 137B; venation, similar to lamina. Developing and fully expanded leaves, lower surface: 138B; venation, similar to lamina.

Flower description:

*Flower type/habit.*—Single, rounded salverform flowers arranged in terminal and lateral cymes; flowers face upright and outward. Freely flowering habit with about six flowers per inflorescence.

*Fragrance.*—Present; typical of *Phlox*.

*Natural flowering season.*—Continuously flowering from April to late October in Japan. Flowers not persistent.

*Postproduction longevity.*—Flowers last about five days on the plant.

*Inflorescence height.*—About 2.9 cm.

*Inflorescence diameter.*—About 5.7 cm.

*Flower buds.*—Height: About 1.5 cm. Diameter: About 3.1 mm. Shape: Clavate. Color: 1D.

*Flowers.*—Diameter: About 2.9 cm. Depth: About 1.3 cm.

*Petals.*—Quantity per flower: Typically five in a single whorl; petals fused at the base into a narrow tube. Lobe length: About 1.2 cm. Lobe width: About 1.3 cm. Shape: Broadly rhombic. Apex: Cuspidate. Margin: Entire. Aspect: Mostly flat. Texture, upper and lower surfaces: Smooth, glabrous. Color: Developing and fully expanded petals, upper surface: 155A. Developing and fully expanded petals, lower surface: 156A.

*Sepals.*—Quantity per flower: Typically five in a single whorl, fused; narrow tubular calyx. Length: About 4.4 mm. Width: About 0.5 mm. Shape: Lanceolate. Apex: Acute. Texture, upper and lower surfaces: Smooth, glabrous. Color, immature, upper and lower surfaces: 137B. Color, mature, upper and lower surfaces: 137B.

*Pedicels.*—Length: About 3.6 mm. Diameter: About 0.5 mm. Texture: Pubescent. Color: 145B.

*Reproductive organs.*—Stamens: Quantity per flower: Typically five. Anther shape: Linear. Anther length: About 1 mm. Anther color: 12A. Pollen amount: Moderate. Pollen color: 12A. Pistils: Quantity per flower: Typically one. Stigma shape: Tri-parted. Stigma color: 1C. Style length: About 0.4 mm. Style color: 1C. Ovary color: 144A.

*Seed/fruit.*—Seed and fruit development have not been observed.

Disease/pest resistance: Plants of the new *Phlox* have not been noted to be resistant to specific pathogens and pests common to *Phlox*.

Garden performance: Plants of the new *Phlox* have been observed to have good garden performance and tolerate rain, wind and tolerated temperatures from 0 to 35° C.

It is claimed:

1. A new and distinct cultivar of *Phlox* plant named 'Sunphloho', as illustrated and described.

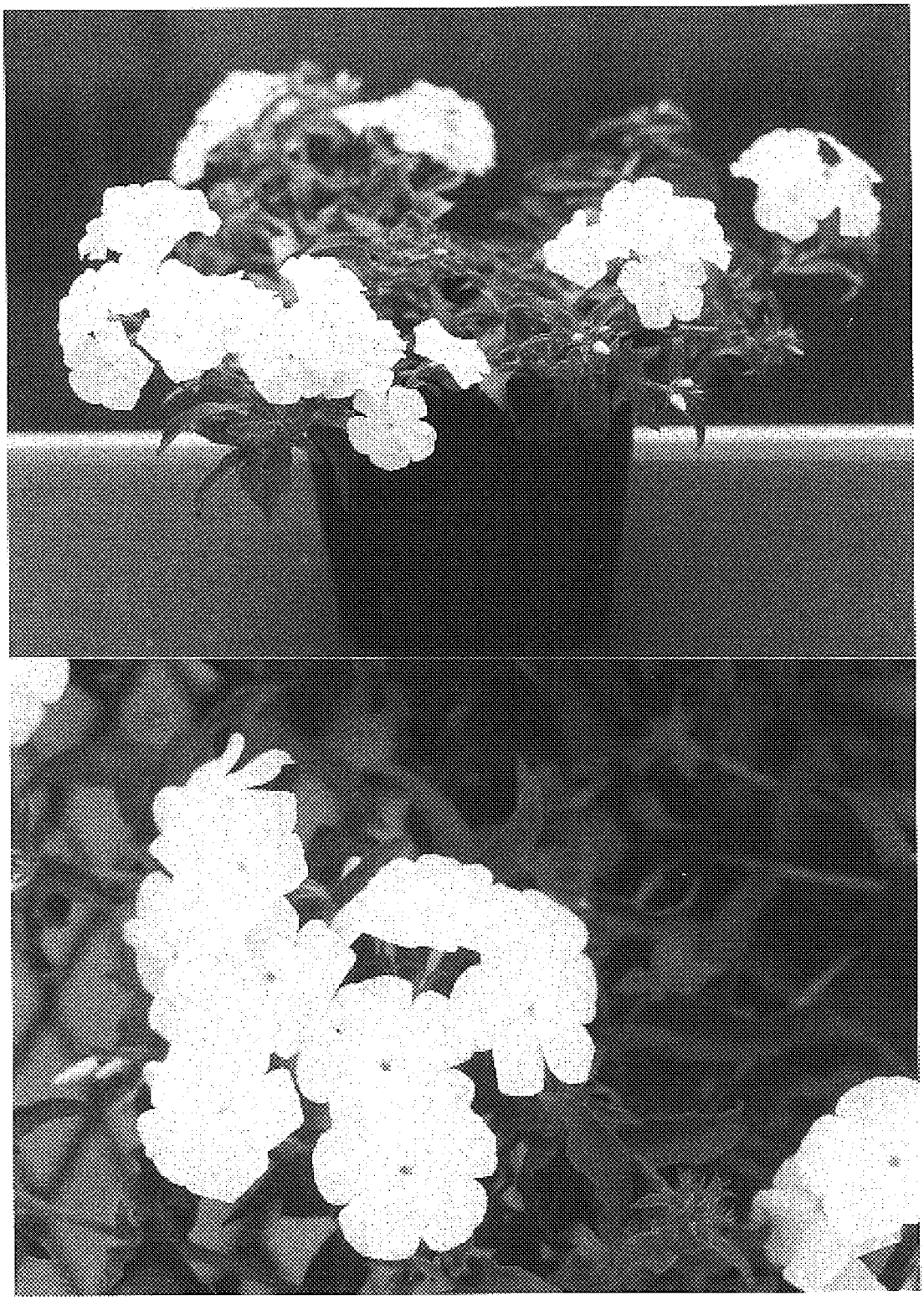

* * * * *